United States Patent [19]
Yoon

[11] Patent Number: 5,603,719
[45] Date of Patent: Feb. 18, 1997

[54] RETRACTABLE SAFETY TROCAR WITH MULTIPLE TRIGGERING AND/OR MOVING COMPONENTS

[76] Inventor: InBae Yoon, 2101 Highland Ridge Dr., Phoenix, Md. 21131

[21] Appl. No.: 374,380

[22] Filed: Jan. 18, 1995

Related U.S. Application Data

[63] Continuation-in-part of Ser. No. 247,205, May 20, 1994, and Ser. No. 254,007, Jun. 3, 1994, Pat. No. 5,478,317, said Ser. No. 247,205, May 20, 1994, is a division of Ser. No. 800,507, Nov. 27, 1991, abandoned, said Ser. No. 254,007, Jun. 9, 1994, is a continuation of Ser. No. 800,507, Nov. 27, 1991.

[51] Int. Cl.$^6$ ............................................. A61M 5/20
[52] U.S. Cl. ........................................ 606/185; 604/165
[58] Field of Search ........................... 128/751, 752, 128/753, 754; 604/95, 158, 162, 163, 164, 165, 170, 272, 274, 280, 169; 606/167, 171, 185

[56] References Cited

U.S. PATENT DOCUMENTS

| | | |
|---|---|---|
| Re. 32,922 | 5/1989 | Levin et al. . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,442,836 | 4/1984 | Meinecke et al. . |
| 4,488,545 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,670,008 | 6/1987 | Von Albertini . |
| 4,677,979 | 7/1987 | Burns . |
| 4,747,831 | 5/1988 | Kulli . |
| 4,802,275 | 4/1989 | Haber et al. . |
| 4,817,603 | 4/1989 | Turner et al. . |
| 4,869,717 | 9/1989 | Adair . |
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. . |
| 4,931,042 | 6/1990 | Holmes et al. . |
| 4,943,280 | 7/1990 | Lander . |
| 4,946,446 | 8/1990 | Vadher . |

(List continued on next page.)

FOREIGN PATENT DOCUMENTS 2544262  4/1977  Germany .
1435246  11/1988  U.S.S.R. .

*Primary Examiner*—Guy Tucker

[57] ABSTRACT

A safety penetrating instrument for establishing a portal in the wall of an anatomical cavity includes a housing, a distally-biased portal sleeve movable proximally during penetration from an extended rest position to a retracted position, a penetrating member disposed within the portal sleeve and movable relative thereto between an extended position where a distal end of the penetrating member protrudes from the portal sleeve distal end and a retracted position where the penetrating member distal end is proximally spaced from the portal sleeve distal end, a retracting mechanism for moving the penetrating member from the penetrating member extended position to the penetrating member retracted position, a locking mechanism for locking the penetrating member in the penetrating member extended position while permitting a predetermined amount of proximal movement of the penetrating member during penetration of the anatomical cavity wall, a penetrating member bias member for biasing the penetrating member distally in the penetrating member extended position while permitting the penetrating member to move proximally during penetration of the anatomical cavity wall, and a releasing mechanism responsive to penetration of the anatomical cavity wall for triggering release of the locking mechanism to permit the retracting mechanism to move the penetrating member proximally to the penetrating member retracted position.

11 Claims, 4 Drawing Sheets

U.S. PATENT DOCUMENTS

| | | |
|---|---|---|
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deniega et al. . |
| 5,104,382 | 4/1992 | Brinkerhoff et al. . |
| 5,104,383 | 9/1992 | Shichman . |
| 5,114,407 | 5/1992 | Burbank . |
| 5,116,353 | 5/1992 | Green . |
| 5,127,909 | 7/1992 | Shichman . |
| 5,129,885 | 7/1992 | Green et al. . |
| 5,152,754 | 10/1992 | Plyley et al. . |
| 5,158,552 | 10/1992 | Borgia et al. . |
| 5,207,647 | 5/1993 | Phelps . |
| 5,226,426 | 7/1993 | Yoon . |
| 5,226,891 | 7/1993 | Bushatz et al. . |
| 5,290,243 | 3/1994 | Chodorow et al. . |
| 5,290,304 | 3/1994 | Storace . |
| 5,295,993 | 3/1994 | Green . |
| 5,312,354 | 5/1994 | Allen et al. . |
| 5,318,580 | 6/1994 | Gresl, Jr. . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,342,382 | 8/1994 | Brinkerhoff et al. . |
| 5,346,459 | 9/1994 | Allen . |
| 5,350,393 | 9/1994 | Yoon . |
| 5,360,405 | 11/1994 | Yoon . |
| 5,372,588 | 12/1994 | Farley et al. . |
| 5,376,082 | 12/1994 | Phelps . |

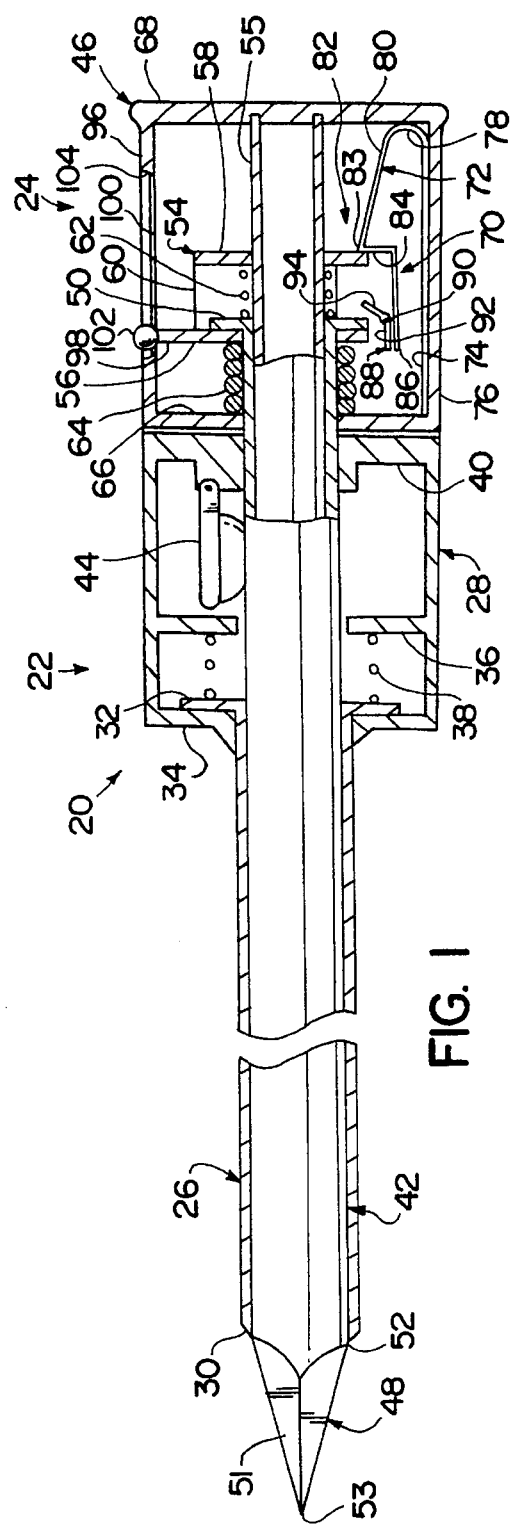
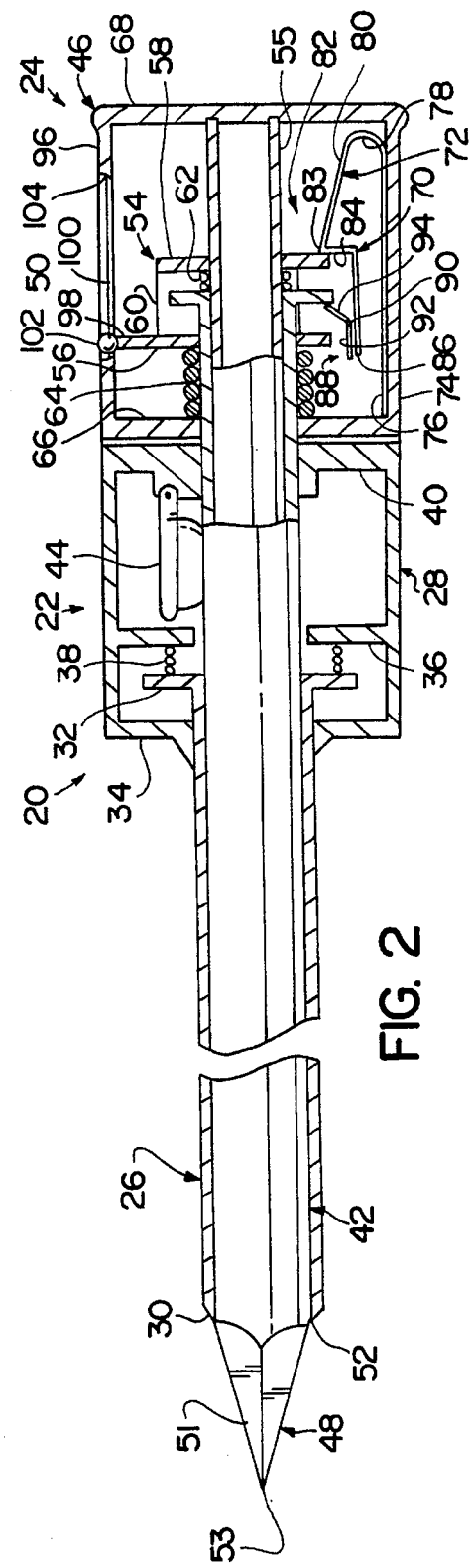

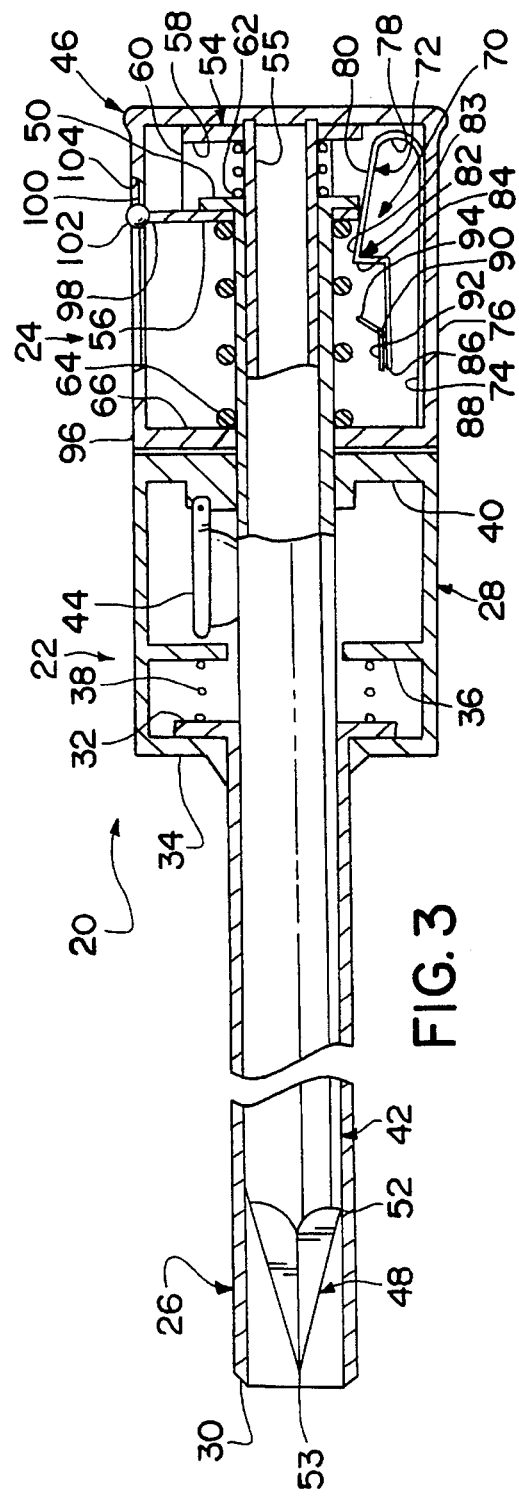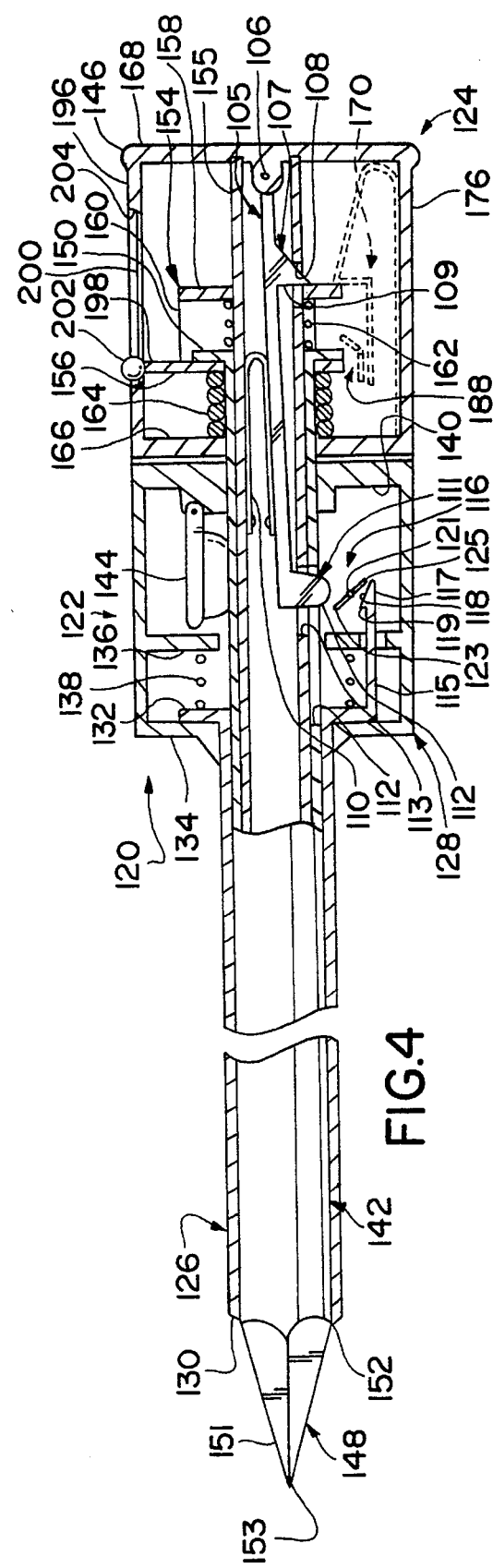

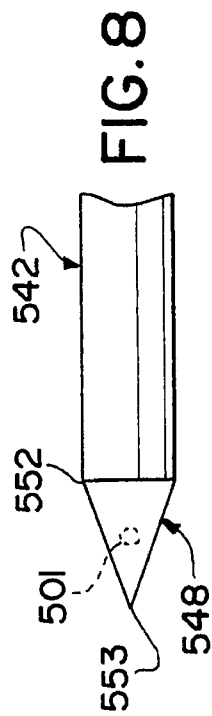
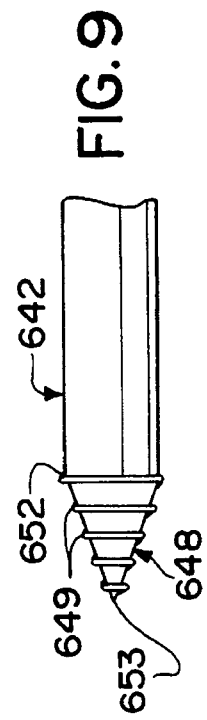
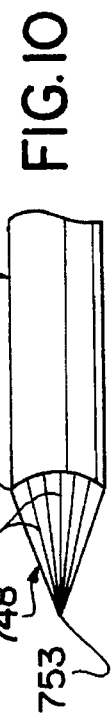
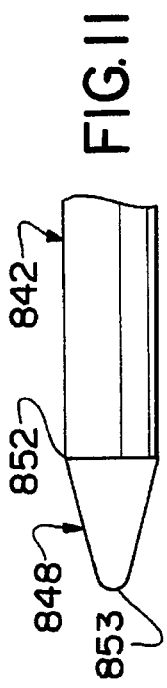
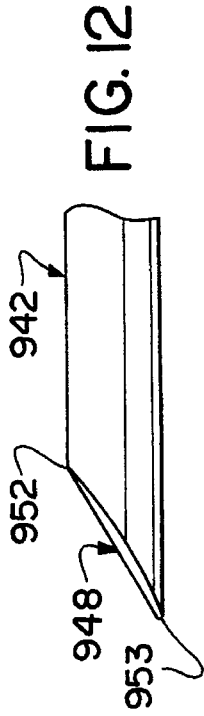
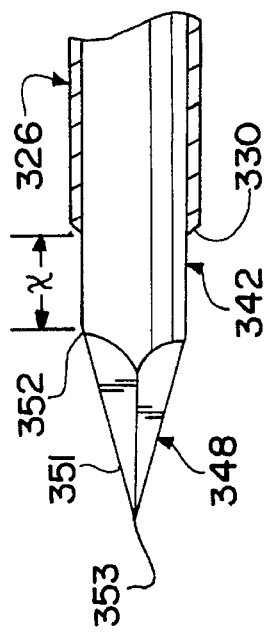
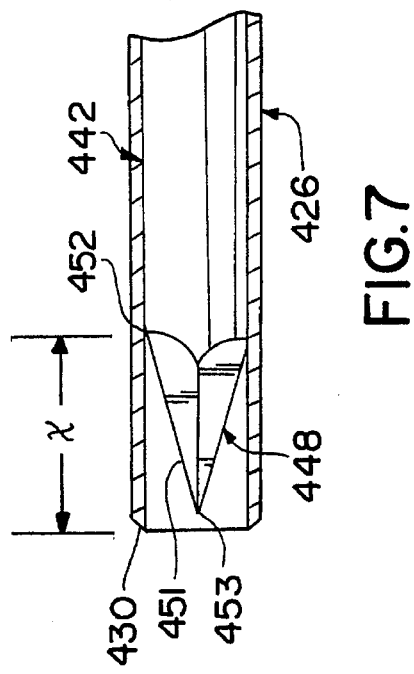

RETRACTABLE SAFETY TROCAR WITH MULTIPLE TRIGGERING AND/OR MOVING COMPONENTS

CROSS-REFERENCE TO RELATED APPLICATIONS

This application is a continuation-in-part of pending application Ser. Nos. 08/247,205, filed May 20, 1994, still pending, and Ser. No. 08/254,007, filed Jun. 3, 1994, now U.S. Pat. No. 5,478,517, which are a divisional application and a continuation application, respectively, of application Ser. No. 07/800,507, filed Nov. 27, 1991 and now abandoned. The disclosures of the above patent applications are incorporated herein by reference.

BACKGROUND OF THE INVENTION

1. Field of the Invention

The present invention pertains to safety penetrating instruments and, more particularly, to safety penetrating instruments for use in forming portals for establishing communication with anatomical cavities wherein tissue and organ structures are protected from the tips of the penetrating members and to methods of penetrating anatomical cavity walls with safety penetrating instruments.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laparoscopic procedures in the abdominal cavity. Such penetrating instruments typically include a cannula or portal sleeve and a penetrating member, such as a trocar, disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring-biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While retracting safety penetrating instruments have been well received, there is room for improvement in easing penetration and minimizing the likelihood of the penetrating member being retracted before the portal sleeve has entered the anatomical cavity.

SUMMARY OF THE INVENTION

Accordingly, it is a primary object of the present invention to improve safety penetrating instruments of the type having a portal sleeve and a retractable penetrating member.

An additional object of the present invention is to permit both the penetrating member and portal sleeve of a safety penetrating instrument to move proximally in response to tissue contact during penetration of an anatomical cavity wall.

It is another object of the present invention to maintain distal ends of the penetrating member and portal sleeve of a safety penetrating instrument in substantially aligned positions to create a smooth distal profile as the penetrating member and portal sleeve are moved proximally in response to tissue contact during penetration of an anatomical cavity wall.

A further object of the present invention is to minimize the likelihood of the penetrating member of a safety penetrating instrument being retracted before the portal sleeve has entered an anatomical cavity by conditioning retraction of the penetrating member on distally-biased movement of both the penetrating member and the portal sleeve in response to a reduction in force from tissue contact upon entering the anatomical cavity.

Some of the advantages of the present invention over the prior art are that penetration of an anatomical cavity wall can be achieved using a smooth and continuous movement, that penetration of an anatomical cavity wall can be commenced with the portal sleeve in an extended rest position either shielding or exposing the tip of the penetrating member as desired, and that retraction of the penetrating member of the safety penetrating instrument can be achieved with a single trigger mechanism or with multiple trigger mechanisms for varying degrees of redundancy such that the safety and efficacy of the safety penetrating instrument is enhanced.

The present invention is generally characterized in a safety penetrating instrument for establishing a portal in the wall of an anatomical cavity including a housing, an elongate portal sleeve movable relative to the housing between an extended rest position and a retracted position and having a proximal end mounted by the housing and a distal end for introduction in the anatomical cavity, portal sleeve bias means for biasing the portal sleeve distally toward the portal sleeve extended position, a penetrating member disposed within the portal sleeve and movable relative thereto between an extended position where a distal end of the penetrating member protrudes from the portal sleeve distal end and a retracted position where the penetrating member distal end is proximally spaced from the portal sleeve distal end, retracting means for moving the penetrating member from the penetrating member extended position to the penetrating member retracted position, means for manually moving the penetrating member from the penetrating member retracted position to the penetrating member extended position, locking means for locking the penetrating member in the penetrating member extended position while permitting a predetermined amount of proximal movement of the penetrating member during penetration of the anatomical cavity wall, penetrating member bias means for biasing the penetrating member distally in the penetrating member extended position while permitting the penetrating member to move proximally from the penetrating member extended position during penetration of the anatomical cavity wall, and releasing means responsive to penetration of the safety penetrating instrument into the anatomical cavity for triggering release of the locking means to permit the retracting means to move the penetrating member to the penetrating member retracted position. The releasing means of the safety penetrating instrument can be responsive to distally-biased movement of the penetrating member, the portal sleeve or both the penetrating member and the portal sleeve for triggering release of the locking means to permit retraction of the penetrating member.

Other objects and advantages of the present invention will become apparent from the following description of the preferred embodiments taken in conjunction with the accompanying drawings wherein, unless specified otherwise, like parts or parts that perform like functions are identified in each of the several figures by the same reference numerals or by reference numerals sharing the same last two digits.

BRIEF DESCRIPTION OF THE DRAWINGS

FIG. 1 is a broken side view, partly in section, of a safety penetrating instrument according to the present invention.

FIG. 2 is a broken side view, partly in section, of the safety penetrating instrument of FIG. 1 during penetration of an anatomical cavity wall.

FIG. 3 is a broken side view, partly in section, of the safety penetrating instrument of FIG. 1 following penetration into an anatomical cavity wall.

FIG. 4 is a broken side view, partly in section, of a modification of the safety penetrating instrument according to the present invention.

FIG. 6 is a fragmentary side view, partly in section, of an alternative distal end alignment for a safety penetrating instrument according to the present invention.

FIG. 7 is a fragmentary side view, partly in section, of another alternative distal end alignment for a safety penetrating instrument according to the present invention.

FIGS. 8–12 are fragmentary side views of modified distal ends for the penetrating member of a safety penetrating instrument according to the present invention.

DESCRIPTION OF THE PREFERRED EMBODIMENTS

Figure 5:
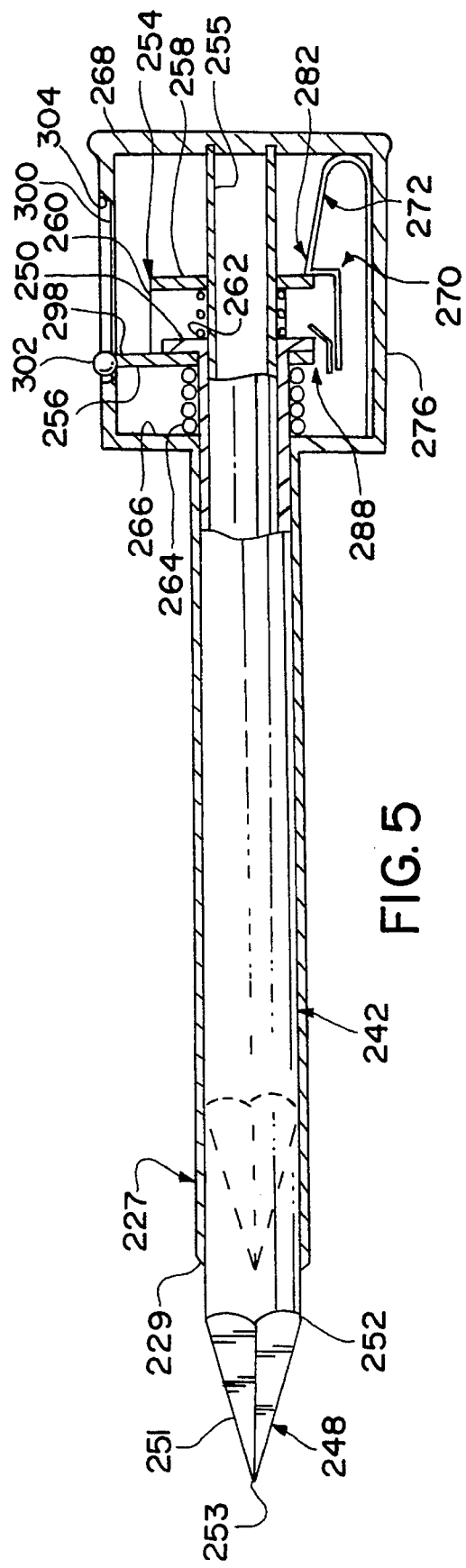
FIG. 5 is a side view, partly in section, of a modified penetrating unit for use with a safety penetrating instrument according to the present invention.

A safety penetrating instrument 20 according to the present invention, as shown in FIG. 1, is formed of a portal unit 22 and a penetrating unit 24. The portal unit 22 can be made of any desirable, medical grade materials depending on procedural use and desirability of being for single patient use or re-usable. The portal unit includes an elongate portal sleeve 26 and a housing 28 mounting a proximal end of the portal sleeve 26. Portal sleeve 26 terminates distally at a distal end 30 and proximally at a flange 32 disposed between front wall 34 of the housing 28 and an inner wall or partition 36 proximally spaced from the front wall. A bias member 38, in the form of a helical coil spring disposed around the longitudinal axis of the safety penetrating instrument and mounted in compression between the portal sleeve flange 32 and the partition 36, biases the portal sleeve 26 distally to cause flange 32 to abut the front wall of the housing. It will be appreciated, however, that other types of bias members can be used, including tension springs, compression springs, torsion springs, pan springs, rubber, plastic or magnets, for example.

Portal sleeve 26 can have any desirable cross-sectional configuration, including cylindrical or tubular configurations, in accordance with the procedure to be performed and the anatomical cavity to be penetrated. Preferably, portal sleeve 26 is made of a substantially cylindrical length of rigid or flexible and transparent or opaque material, such as stainless steel or other medically acceptable plastic or metal material, and has a tubular configuration defining a lumen between the distal and proximal portal sleeve ends for receiving a penetrating member 42 of penetrating unit 24. The portal sleeve distal end 30 can have various configurations to protect tissue within an anatomical cavity by covering the distal tip of the penetrating member with the portal sleeve in the portal sleeve extended position; and, as shown, the portal sleeve distal end defines an annular or peripheral edge having a relatively blunt or chamfered configuration to ease penetration while protecting tissue within the anatomical cavity. The portal sleeve can be provided with a shape or surface texture to increase resistance of the portal sleeve to passage through anatomical tissue such that the portal sleeve moves proximally against the bias of spring 38 during penetration of anatomical tissue by the safety penetrating instrument. The resistance of the portal sleeve can be increased in many various ways such as by roughening, texturing or dimpling the external surface of the portal sleeve or by providing the external surface with bumps, threads, ridges or other irregularities or by configuring the portal sleeve to have a slight enlargement or protrusion.

Housing 28 can be made of any desirable material and can have any desirable configuration to facilitate grasping by a surgeon and includes a rear wall 40 having an opening therein aligned with an opening in the housing front wall 34 to allow passage therethrough by the penetrating member 42. The housing 28 is preferably constructed to sealingly engage instruments passing therethrough and to include a valve 44 biased to a closed state when no instrument passes through the portal sleeve. A flapper valve 44 is shown; however, any suitable valve construction can be utilized, including trumpet or nipple valves.

Penetrating unit 24 includes penetrating member 42 and a hub 46 mounting the proximal end of the penetrating member. The penetrating member 42 terminates distally at a distal end 48 and proximally at a transverse flange 50 disposed between walls of a rail member 54 mounted in the hub 46. The proximal end of the penetrating member 42 includes a hollow portion telescopically fitted over a cylindrical guide tube 55 extending distally from the rear wall 68 of the hub. The penetrating member distal end 48 includes a plurality of facets 51 which extend distally from a proximal base or junction 52 to form a sharp tissue penetrating tip 53. Rail member 54 is movable within hub 46 and is generally U-shaped including a forward wall 56 disposed transverse or perpendicular to a longitudinal axis of the penetrating instrument, a rearward wall 58 in configuration parallel to forward wall 56 and a side wall 60 transversely joining the forward and rearward rail member walls. Flange 50 is disposed between the rail member forward and rearward walls with the rail member forward wall 56 having an opening therein allowing passage therethrough by the penetrating member 42. The rail member forward and rearward walls are disposed parallel or substantially parallel to flange 50, and a bias member 62 is connected between penetrating member flange 50 and the rail member rearward wall 58 to bias the penetrating member distally. As shown, bias member 62 includes a helical coil spring disposed around the guide tube 55 and mounted in compression between flange 50 and the rail member rearward wall 58 to bias the penetrating member 42 distally to cause flange 50 to abut the rail member forward wall 56. However, bias member 62 can include various other types of springs as well as other types of bias devices including compression springs, tension springs, torsion springs, pan springs, leaf springs, rubber, plastic or magnets, for example. A retracting member 64 is mounted between rail member forward wall 56 and a front wall 66 of hub 46 to bias the penetrating member 42 in a proximal direction to a retracted position where distal end 48 of the penetrating member is disposed proximally of the portal sleeve distal end 30 as will be explained further below. The retracting member includes a helical coil spring disposed around the penetrating member 42 and mounted in compression between the rail member forward wall 56 and the front wall 66 of the hub to bias the rail member 54 and, therefore, the penetrating member 42, in a proximal direction to a retracted position where the distal end 48 of the penetrating member is disposed proximally of the portal sleeve distal end.

A locking and releasing mechanism 70 for locking the penetrating member in an extended position, shown in FIG. 1, exposing the distal end 48 of the penetrating member and for releasing the rail member 54 to allow the penetrating member 42 to move to the retracted position includes a latch or locking spring 72, made of a strip of resilient material, formed to have a substantially flat base 74 secured to a bottom wall 76 of hub 46 and a bend 78 joining the proximal end of the base 74 with an upwardly angled arm 80 spaced from the base. Arm 80 carries or forms a latch 82 having a proximal angled latching surface 83 joining a distal latching surface 84 disposed substantially transverse to the longitudinal axis of the safety penetrating instrument and substantially parallel to the rail member forward wall 56. Arm 80 has an extension 86 positioned distally of latch 82, and a releasing member or trigger 88 is juxtaposed with extension 86. The trigger 88 is pivotally mounted in the hub on a pin 90 secured to a wall or walls of the hub or structure supported in the hub, and the trigger is generally L-shaped with a leg 92 overlying extension 86 and a leg 94 extending transversely from leg 92 but at a slight angle toward the proximal end of the safety penetrating instrument. A torsion spring (not shown) is coiled around pin 90 and fixed to trigger 88 to bias the trigger counterclockwise, looking at FIG. 1, such that leg 92 is biased toward extension 86.

Rail member forward wall 56 extends toward a top wall 96 of the hub and a post 98 extends from the rail member forward wall through a longitudinal slot 100 formed in the top wall of the hub to terminate at a handle or knob 102 disposed within an elongate trough-like recess 104. Handle 102 can be grasped and manually moved distally along the slot formed in the top wall of the hub to move the penetrating member from the retracted position to the locked extended position as previously explained above.

The portal unit 22 and the penetrating unit 24 can be provided separately or assembled together as shown in FIG. 1, and either or both of the portal and penetrating units can be manufactured in a manner to be disposable for single patient use or to be sterilizable for re-use. The hub 46 can be coupled to the housing 28 by suitable detent or latch mechanisms if desired, and the penetrating unit can be withdrawn from the portal unit leaving the portal sleeve 26 in place within an anatomical cavity.

In use, the safety penetrating instrument 20 can be provided in the condition illustrated in FIG. 3 with the portal sleeve 26 in the extended rest position and the penetrating member 42 in the retracted position where the distal end 48 of the penetrating member is proximally spaced from the distal end 30 of the portal sleeve to protect the sharp tip 53 of the penetrating member. In order to move the penetrating member to the extended position shown in FIG. 1, the handle 102 is grasped to move the rail member 54, and thus the penetrating member 42, distally until the rail member rearward wall 58 rides over latch 82 to be latched in the extended position with the rail member rearward wall 58 locked against distal latching surface 84. The user can feel the rail member rearward wall 58 lock into place in engagement with the latch 82 and can also visually determine that the penetrating member is in the locked extended position by noting the position of the handle 102 at a distal end of the slot 100.

With the penetrating member 42 locked in the extended position illustrated in FIG. 1, the portal sleeve distal end 30 can be disposed proximally of the distal tip 53 of the penetrating member in alignment with the transverse dimensional transition or junction 52 to present a smooth profile for penetrating tissue. Penetrating member 42 can move proximally against the bias of bias member 62 in the extended position in response to forces acting on the penetrating member distal end, such as the force from tissue contact during penetration of an anatomical cavity wall. Proximal movement of the penetrating member is limited by engagement of the penetrating member flange 50 with the rearward wall 58 of the rail member, which serves as a stop or abutment. Similarly, portal sleeve 26 can move proximally against the bias of bias member 38 in response to forces acting on the portal sleeve distal end 30 until the portal sleeve flange 32 abuts the housing partition 36. Since both the portal sleeve and the penetrating member are free to move proximally in response to tissue resistance during penetration, the alignment of the portal sleeve distal end with the penetrating member junction can be substantially maintained in order to ease penetration. When penetration of an anatomical cavity wall is commenced, therefore, the force from tissue contact on the portal sleeve and penetrating member distal ends 30 and 48 will cause the portal sleeve and penetrating member to move together proximally against the bias of respective bias members 38 and 62. Penetrating member flange 50 will also move past trigger leg 94. Movement of flange 50 proximally past trigger leg 94 does not cause movement of latch 82 since there is no contact of trigger leg 92 with arm extension 86; and, accordingly, flange 50 is then positioned proximally of trigger leg 94 as shown in FIG. 2.

Upon entry into the anatomical cavity, the counterforce on the portal sleeve and penetrating member distal ends caused by tissue contact will be reduced allowing bias members 38 and 62 to move the portal sleeve and penetrating member distally. Distal movement of the penetrating member causes flange 50 to engage trigger leg 94 and to pivot the trigger counterclockwise looking at FIG. 2 causing leg 92 to engage arm extension 86. The engagement of leg 92 with arm extension 86 causes arm 80 to move toward base 74 moving the latch 82 out of engagement with the rail member rearward wall 58 thereby allowing the retracting member 64 to cause the penetrating member to move proximally to the retracted position wherein the penetrating member distal end 48 is proximally spaced from the portal sleeve distal end 30 to protect the sharp tip 53 of the penetrating member as shown in FIG. 3. The penetrating unit 24 including the penetrating member 42 can then be withdrawn from the portal unit 22 leaving the portal sleeve 26 in place within the anatomical cavity wall to serve as a portal for introducing medical instruments therethrough.

A modification of the safety penetrating instrument of the present invention is shown in FIG. 4 at 120. The modified safety penetrating instrument 120 is similar to safety penetrating instrument 20 except that movement of the penetrating member to the retracted position is triggered by distally-biased movement of the portal sleeve in response to a reduction in the force from tissue contact following entry into the anatomical cavity. Safety penetrating instrument 120 includes a portal unit 122 and a penetrating unit 124 having a penetrating member 142 and a hub 146 mounting a proximal end of the penetrating member. Penetrating member 142 is similar to penetrating member 42 and terminates distally at a distal end 148 and proximally at a transverse flange 150 disposed between forward and rearward walls 156 and 158 of a rail member 154. The proximal end of the penetrating member 142 also includes a hollow portion telescopically fitted over a guide tube 155 extending distally from the rear wall 168 of the hub 146. The bias member 162 is similar to bias member 62 and is disposed around the guide tube 168 and held in compression between the penetrating member flange 150 and the rearward wall of rail member 154. A retracting member 164, similar to retracting member 64, is disposed around the penetrating member 142 and is held in compression between the rail member forward wall 156 and hub forward wall 166.

Rail member 154 is locked in the extended position shown in FIG. 4 by a longitudinal latch arm 105 disposed within the guide tube 155 and having a proximal end pivotally mounted on a pin 106 secured to the rear wall 168 of the hub. Latch arm 105 carries a latching protrusion 107 in opposed relation to a slot 108 formed in the guide tube 155. Protrusion 107 is generally triangular with a transverse latching surface 109 configured to extend through slot 108 formed in the guide tube 155 to engage the rail member rearward wall 158. A leaf spring 110 is connected between the latch arm 105 and an inner surface of the guide tube 155 to bias the arm 105 in a counterclockwise direction looking at FIG. 4 toward an engaged position where latching protrusion 107 extends through the slot 108 formed in the guide tube. A triggering protrusion 111 is formed at a distal end of the latch arm 105 and includes a curved distal edge 112 that protrudes through aligned slots 113 and 114 formed in the guide tube 155 and the penetrating member 142 distally of slot 108 to communicate into housing 128. Penetrating member slot 114 is sufficiently long to allow back and forth movement of the penetrating member 142 within the rail member 154.

Portal unit 122 is similar to portal unit 22 for safety penetrating instrument 20 and, in addition, includes a finger 115 extending perpendicularly from the portal sleeve flange 132 in a proximal direction and a lever 116 disposed between finger 112 and triggering protrusion 111. Finger 115 terminates proximally in a barb or pawl 117 with an acutely angled leading edge 118 and a vertical trailing edge 119 parallel to flange 132. Lever 116 is pivotally mounted on a pin 121 secured to a wall or walls of housing 128 perpendicular to the longitudinal axis of the penetrating instrument, and includes axially opposed ends 123 and 125. Finger 115 is positioned on flange 132 in a manner to engage lower end 125 of lever 116 when moved proximally. Upper end 123 of lever 116 is rotatable in a clockwise direction to contact triggering protrusion 111.

Use of the safety penetrating instrument 120 is similar to that described above with respect to safety penetrating instrument 20 in that, when the user desires to penetrate into an anatomical cavity, the safety penetrating instrument will normally be provided with the penetrating member 142 in the retracted position where the distal end 148 of the penetrating member is proximally spaced from the portal sleeve distal end 130. Additionally, the portal sleeve 126 will be provided in a rest position where the portal sleeve flange 132 abuts the housing front wall 134. Furthermore, latching protrusion 107 of latch arm 105 will be disposed distally of the rail member rearward wall 158 and barb 117 of finger 115 will be disposed distally of lever lower end 125. The penetrating member 142 is biased to the retracted position by retracting member 164 with handle 202 being disposed at a proximal end of the slot 200 in the hub 146.

Prior to commencing penetration of an anatomical cavity wall, handle 202 is grasped and manually moved distally to move penetrating member 142 distally against the bias of retracting member 164 until the rail member rearward wall 158 rides over the latching protrusion 107 by engaging an angled proximal surface of the latching protrusion 107 to move the latch arm 105 clockwise looking at FIG. 4. When rail member rearward wall 158 moves distally past latching surface 109, latch arm 105 springs back in a counterclockwise direction to lock the rail member 154 and penetrating member 142 mounted thereby in the extended position shown. As previously noted, the user can feel the rail member lock into place in engagement with latch arm 105 and can also visually determine that the penetrating member is in the locked extended position by noting the position of the handle 202 at a distal end of the slot. With the penetrating member 142 locked in the extended position, penetrating member flange 150 will be distally biased by bias member 162 into abutting relation with the rail member forward wall 156. The portal sleeve flange 132 will also be distally biased by bias member 138 into abutment with housing forward wall 134 such that the distal end 130 of the portal sleeve will be disposed adjacent the transverse dimensional transition or junction 152 of the penetrating member 142.

With the safety penetrating instrument 120 in the position illustrated in FIG. 4, penetration of the anatomical cavity wall is commenced, and the force from tissue contact on the portal sleeve and penetrating member distal ends 130 and 148 will cause the portal sleeve and penetrating member to move together proximally against the bias of springs 138 and 162, respectively. Proximal movement of the portal sleeve 126 also causes barb 117 carried by finger 115 to contact and move past lever lower end 125 causing lever 116 to rotate counter-clockwise. Lever upper end 123 is thus moved away from triggering protrusion 111 without causing any movement of latch arm 105. Accordingly, the barb 117 will then be positioned proximally of the lever lower end 125. Upon entry into the anatomical cavity, the counter force on the distal end of the portal sleeve will be reduced allowing spring 138 to move the portal sleeve distally causing barb 117 to engage lever lower end 125 and thereby to pivot the lever 116 clockwise causing lever upper end 123 to engage triggering protrusion 111. The engagement of lever 116 with triggering protrusion 111 causes latch arm 105 to rotate clockwise, looking at FIG. 4, moving the latching protrusion 107 out of engagement with rail member rearward wall 158 thereby allowing retracting member 164 to cause the penetrating member to move proximally to the retracted position shown in FIG. 3 wherein the penetrating member distal end 148 is proximally spaced from the distal end 130 of the portal sleeve 126 to protect the sharp tip 153 of the penetrating member. The penetrating unit 124 can then be withdrawn from the portal unit 122 leaving the portal sleeve 126 in place for the introduction of medical instruments therethrough.

Another modification of the safety penetrating instrument of the present invention is arrived at by combining the locking and releasing mechanisms of safety penetrating instruments 20 and 120 to permit movement of the penetrating member to the retracted position in response to distally-biased movement of both the portal sleeve and penetrating member. The modification involves mounting a locking and releasing mechanism such as locking and releasing mechanism 70 for engaging the rail member 154 in hub 148 of safety penetrating instrument 120 as shown in phantom at 170 in FIG. 4. Use of the modified safety penetrating instrument is similar to that described above in connection with safety penetrating instruments 20 and 120 with the exception of both the latch spring 72 and latch arm 105 must be disengaged in order for the penetrating member 142 to be moved proximally to the retracted position.

A modified penetrating unit for the safety penetrating instrument of the present invention is shown in FIG. 5 at 224. The modified penetrating unit 224 is similar to penetrating unit 24 for safety penetrating instrument 20 but with a protective sheath or sleeve 227 fixed to the front wall 266 of the hub 246. The protective sheath 227 extends distally from the front wall of the hub to terminate distally at a distal end 229. Penetrating member 242 is disposed within the protective sheath 227 and, when the penetrating member is in the locked extending position shown, the distal end 248 of the penetrating member is distally spaced from the distal end 229 of the protective sheath such that the distal end 229 of the protective sheath is proximally spaced from the transverse dimensional transition or junction 252 of the penetrating member 242 so that the penetrating member can move into alignment with the protective sheath to ease penetration. With the penetrating member in the retracted position, shown in phantom in FIG. 5, the distal end 248 of the penetrating member is proximally spaced from the distal end 229 of the protective sheath so that the sharp distal tip 253 of the penetrating member is protected by the sheath when the penetrating unit 224 is removed from a portal unit such as portal unit 22.

In the embodiments shown, the distal end of the portal sleeve is aligned with a transverse dimensional transition or junction of the penetrating member when the portal sleeve is in a rest position and the penetrating member is locked in the extended position prior to being used for penetrating an anatomical cavity wall; and since the penetrating member and portal sleeve are movable during penetration, the distal ends of the penetrating member and portal sleeve become displaced proximally relative to the housing and hub, with distally-biased movement of at least one of the penetrating member and portal sleeve triggering release of a latching mechanism to allow a retracting member to move the penetrating member proximally to a retracted position where the tip of the penetrating member is protected.

FIG. 6 shows an alternative distal configuration for the safety penetrating instruments of the present invention wherein the distal end 330 of the portal sleeve is proximally spaced from the distal end junction 352 of the penetrating member 342 a predetermined distance x when the portal sleeve is in the rest position and the penetrating member is locked in the extended position. In this configuration, the penetrating member will move proximally during penetration towards becoming aligned with the portal sleeve distal end to ease penetration by providing a smooth profile and will either stop or move together with the portal sleeve as penetration continues. Upon entering into an anatomical cavity, both the penetrating member and the portal sleeve will spring back toward their original positions with the distally-biased movement of one or both of the portal sleeve and penetrating member triggering release of the latch holding the penetrating member to permit the retracting member to move the penetrating member proximally to the retracted position where the sharp tip 353 of the penetrating member is protected.

Another distal configuration for the safety penetrating instruments of the present invention is shown in FIG. 7 wherein the distal end 430 of the portal sleeve is distally spaced from the distal end junction 452 of the penetrating member 442 a predetermined distance x when the portal sleeve is in the rest position and the penetrating member is locked in the extended position. In this configuration, the portal sleeve will move proximally during penetration towards becoming aligned with the penetrating member distal end junction to ease penetration by providing a smooth profile and will move together with the penetrating member as penetration continues. Upon entering into an anatomical cavity, both the penetrating member and the portal sleeve will spring back toward their original positions with the distally-biased movement of one or both of the portal sleeve and penetrating member triggering release of the latch holding the penetrating member to permit the retracting member to move the penetrating member proximally to the retracted position where the sharp tip 453 of the penetrating member is protected.

From the above, it will be appreciated that the portal sleeve and penetrating member of the safety penetrating instrument of the present invention are movable proximally during penetration of an anatomical cavity wall and distally upon entering the anatomical cavity to trigger retraction of the penetrating member to a position where the distal end of the penetrating member is protected. Retraction of the penetrating member can be conditioned upon distally-biased movement of the portal sleeve, the penetrating member or both the portal sleeve and the penetrating member depending on the type and number of locking and releasing mechanisms. Furthermore, distal ends of the portal sleeve and the penetrating member can be aligned prior to penetration to define a smooth distal profile for penetrating anatomical tissue, which profile can be substantially maintained during penetration by permitting proximal movement of the penetrating member and the portal sleeve. Alternatively, the distal end of the portal sleeve can be distally or proximally spaced from the penetrating member distal end such that movement of the portal sleeve and/or penetrating member in response to tissue contact will cause the distal ends of the portal sleeve and penetrating member to become aligned. If the portal sleeve distal end is distally spaced from the penetrating member distal end in the extended rest position, the portal sleeve will also function as a safety member to protect the penetrating member distal end even in the event that the penetrating member is not retracted.

The components of the safety penetrating instrument of the present invention can be made of any suitable, medical grade materials to permit sterilization for re-use or for single patient use. The components can be made of multiple parts of various configurations and materials to reduce cost. The portal unit can have various valves, stop cocks and seals in the housing to control fluid flow therethrough, and conventional detent mechanisms can be used to connect or latch the hub with the housing when the portal unit and the penetrating unit are assembled. The distal end of the portal sleeve can be chamfered or blunt, smooth or roughened, or have any other configuration depending on the need for ease of penetration or increased resistance. The strength of the bias members biasing the portal sleeve and penetrating member can be chosen according to differences in the resistant forces acting on the portal sleeve and penetrating member in order to maintain a smooth distal profile during penetration.

The distal end of the penetrating member can have any configuration desired for a particular procedure, for example, the pyramidal trocar configuration shown or a conical distal end 548 tapering from a junction 552 to a tip 553 as shown in FIG. 8, a screw-type distal end 648 having helical threads 649 as shown in FIG. 9, a multifaceted distal end 748 having two or more facets 749 as shown in FIG. 10, a blunt distal end 848 having a generally conical shape with a rounded or flattened tip 853 as shown in FIG. 11, or a beveled distal end 948 as shown in FIG. 12. Additionally, the surface defining the distal end of the penetrating member can be irregular or smooth, continuous or disjointed, provided with cutting features or having any combination of the above. Any of the penetrating members shown and described herein can include a viewing port, like the viewing port shown in phantom at 501 in FIG. 8, for accommodating conventional optical viewing systems such as those utilizing fiber optics so that tissue can be visualized during penetration.

The rail member can have various configurations to engage the latch and be released by the trigger. Preferably, the rail member will have a configuration to serve as a stop or abutment for the penetrating member as exemplified herein by a U-shaped rail member.

The locking and releasing mechanisms require only a latch for locking the penetrating member in the extended position and a trigger for releasing the latch in response to distal movement of an operating member such as a flange carried by the penetrating member and/or portal sleeve; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety penetrating instrument of the present invention are disclosed in U.S. Pat. Nos. 5,330,432; 5,324, 268; 5,320,610; 5,336,176; and 5,360,405 to Yoon and Applicant's pending application Ser. Nos. 07/848,838, filed Mar. 10, 1992; 07/845,177, filed Sep. 15, 1992; 07/945,177, filed Sep. 15, 1992; 08/079,586, filed Jun. 22, 1993; 08/195, 512, filed Feb. 14, 1994; 08/196,029, filed Feb. 14, 1994; 08/196,027, filed Feb. 14, 1994; 08/195,178, filed Feb. 14, 1994; 08/237,734, filed May 4, 1994; 08/247,205, filed May 20, 1994; 08/254,007, filed Jun. 3, 1994; and 08/260,439, filed Jun. 15, 1994. The disclosures of the above-listed issued patents and pending patent applications are incorporated herein by reference. The issued patents and applications listed above also disclose various bias arrangements useful with the safety penetrating instrument of the present invention. Other locking and releasing mechanisms that can be used in the safety penetrating instrument of the present invention are disclosed in Applicant's pending application Ser. Nos. 08/279,170 and 08/279,172, filed Jul. 22, 1994, the disclosures of which are incorporated herein by reference.

When a latch arm, such as latch arm 105, is disposed within a hollow portion of a penetrating member for engaging the penetrating member, the latch arm can be pivotally mounted at a proximal end to the hub as shown or mounted within the penetrating member or a guide tube for pivotal movement about a center of the arm or about any other portion of the arm. In addition, such a latch arm can be embodied in a spring strip held in compression within the penetrating member or guide tube and configured to form or carry latching and triggering protrusions. Furthermore, when latch arms are disposed within the penetrating member or guide tube, operating members can be carried by the penetrating member and/or portal sleeve on inside surfaces thereof for engaging triggering portions of the latch arms within the penetrating members to release latching portions of the latch arms holding the penetrating members in their extended positions. Latch arms having such features are shown and described in Applicant's pending application Ser. Nos. 08/279,170 and 08/279,172, filed Jul. 22, 1994.

One or more control buttons, such as the control buttons described in Applicant's copending patent application Ser. No. 08/083,220, filed Jun. 24, 1993, can be mounted next to any latch for manually disengaging the latch to prevent locking of the penetrating member in the extended position. Furthermore, additional latches can be provided or existing latches modified to carry pawls or form latching surfaces for locking a penetrating member in the retracted position and can then be released through the use of a control button as described above to permit the penetrating member to be moved distally to the locked extended position prior to use.

It will also be appreciated that after penetration of the safety penetrating instrument into the anatomical cavity, the distally-biased portal sleeve can act as a shock absorber upon inadvertent contact with tissue. The distal bias for the triggering member (i.e., the portal sleeve and/or penetrating member) of the safety penetrating instrument need only be strong enough to allow slight movement of the member during penetration such that the force-to-penetrate can be minimized.

The features of the various embodiments described above can be combined in any manner desired dependent upon the requirements and complexity of the safety penetrating instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in the wall of an anatomical cavity comprising a housing;

an elongate portal sleeve for introducing medical instruments into the anatomical cavity, said portal sleeve having a proximal end mounted by said housing and a distal end for introduction in the anatomical cavity, said portal sleeve being movable proximally relative to said housing during penetration of the anatomical cavity wall from an extended rest position to a retracted position;

portal sleeve bias means for biasing said portal sleeve distally toward said rest position;

a penetrating member disposed within said portal sleeve and having a distal end for penetrating the anatomical cavity wall, said penetrating member being movable relative to said portal sleeve between an extended position where said penetrating member distal end protrudes from said portal sleeve distal end and a retracted position where said penetrating member distal end is proximally spaced from said portal sleeve distal end, said penetrating member being removable from said housing and said portal sleeve;

retracting means for moving said penetrating member from said penetrating member extended position to said penetrating member retracted position;

means for manually moving said penetrating member from said penetrating member retracted position to said penetrating member extended position;

locking means for locking said penetrating member in said penetrating member extended position while permitting a predetermined amount of proximal movement of said penetrating member during penetration of the anatomical cavity wall;

penetrating member bias means for biasing said penetrating member distally in said penetrating member extended position while permitting proximal movement of said penetrating member during penetration of the anatomical cavity wall; and releasing means responsive to penetration of said safety penetrating instrument into the anatomical cavity for triggering release of said locking means to permit said retracting means to move said penetrating member proximally from said penetrating member extended position to said penetrating member retracted position.

2. A safety penetrating instrument as recited in claim 1 wherein said releasing means is responsive to distally-biased movement of said portal sleeve upon penetrating into the anatomical cavity.

3. A safety penetrating instrument as recited in claim 2 wherein at least a portion of said penetrating member is hollow and wherein said locking and releasing means includes a latch arm extending through said hollow portion of said penetrating member and carrying a proximal latching protrusion for engaging said penetrating member to lock said penetrating member in said extended position and a distal triggering protrusion for being engaged by an operating member carried by said portal sleeve to release said latching protrusion from said penetrating member.

4. A safety penetrating instrument as recited in claim 3 wherein said operating member includes a lever pivotally mounted within said housing to engage said triggering protrusion and to be engaged by an arm extending proximally from said portal sleeve.

5. A safety penetrating instrument as recited in claim 1 wherein said releasing means is responsive to distally-biased movement of said penetrating member upon penetrating into the anatomical cavity.

6. A safety penetrating instrument as recited in claim 5 and further comprising a rail member mounting a proximal end of said penetrating member, wherein said proximal end of said penetrating member includes a flange movable within said rail member and said locking and releasing mechanism includes a latch spring engaging said rail member to lock said penetrating member in said extended position and a trigger responsive to distally-biased movement of said penetrating member flange for releasing said latch spring.

7. A safety penetrating instrument as recited in claim 1 wherein said releasing means is responsive to distally-biased movement of said portal sleeve and said penetrating member upon penetrating into the anatomical cavity.

8. A safety penetrating instrument as recited in claim 7 and further comprising a hub and a rail member movably disposed within said hub for mounting a proximal end of said penetrating member, wherein said proximal end of said penetrating member includes a flange movable within said rail member and said locking and releasing mechanism includes a latch spring disposed within said hub for engaging said rail member to lock said penetrating member in said extended position and a trigger responsive to distally-biased movement of said penetrating member flange for releasing said latch spring; and wherein at least a portion of said penetrating member is hollow and said locking and releasing means further includes a latch arm extending through said hollow portion of said penetrating member and carrying a proximal latching protrusion for engaging said rail member to lock said penetrating member in said extended position and a distal triggering protrusion for being engaged by an operating member carried by said portal sleeve to release said latching protrusion from said rail member, wherein said operating member includes a lever pivotally mounted within said housing to engage said triggering protrusion and to be engaged by an arm extending proximally from said portal sleeve.

9. A safety penetrating instrument as recited in claim 1 wherein said penetrating member distal end extends distally from a junction where a transverse dimension of said penetrating member changes and wherein said portal sleeve distal end is aligned with said junction when said penetrating member and said portal sleeve are in said respective extended positions.

10. A safety penetrating instrument as recited in claim 1 wherein said penetrating member distal end extends distally from a junction where a transverse dimension of said penetrating member changes and wherein said portal sleeve distal end is located proximally of said junction when said penetrating member and said portal sleeve are in said respective extended positions.

11. A safety penetrating instrument for establishing a portal in the wall of an anatomical cavity comprising a housing:

an elongate portal sleeve having a proximal end mounted by said housing and a distal end for introduction in the anatomical cavity, said portal sleeve being movable relative to said housing between an extended rest position and a retracted position;

portal sleeve bias means for biasing said portal sleeve distally toward said rest position;

a penetrating member disposed within said portal sleeve and having a distal end for penetrating the anatomical cavity wall, said penetrating member being movable relative to said portal sleeve between an extended position where said penetrating member distal end protrudes from said portal sleeve distal end and a retracted position where said penetrating member distal end is proximally spaced from said portal sleeve distal end;

retracting means for moving said penetrating member from said penetrating member extended position to said penetrating member retracted position;

means for manually moving said penetrating member from said penetrating member retracted position to said penetrating member extended position;

locking means for locking said penetrating member extended position while permitting a predetermined amount of proximal movement of said penetrating member during penetration of the anatomical cavity wall;

penetrating member bias means for biasing said penetrating member distally in said penetrating member extended position while permitting proximal movement of said penetrating member during penetration of the anatomical cavity wall; and releasing means responsive to penetration of said safety penetrating instrument into the anatomical cavity for triggering release of said locking means to permit said retracting means to move said penetrating member proximally to said penetrating member retracted position;

wherein said penetrating member distal end extends distally from a junction where a transverse dimension of said penetrating member changes and wherein said portal sleeve distal end is located distally of said junction when said penetrating member and said portal sleeve are in said respective extended positions.

* * * * *